United States Patent
Fujimura (10) Patent No.: US 9,504,444 B2
(45) Date of Patent: Nov. 29, 2016

(54) ULTRASOUND ENDOSCOPE DISTAL END PORTION TO ACCOMMODATE BEND WIRES AND WIRING SUBSTRATE

(71) Applicant: OLYMPUS CORPORATION, Tokyo (JP)

(72) Inventor: Takanao Fujimura, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/063,695

(22) Filed: Mar. 8, 2016

(65) Prior Publication Data

US 2016/0183914 A1    Jun. 30, 2016

Related U.S. Application Data (63) Continuation of application No. PCT/JP2014/074226, filed on Sep. 12, 2014.

(30) Foreign Application Priority Data

Oct. 10, 2013  (JP) .................................. 2013-212693

(51) Int. Cl.
| | |
|---|---|
| A61B 8/12 | (2006.01) |
| A61B 8/00 | (2006.01) |
| A61B 1/05 | (2006.01) |
| A61B 1/018 | (2006.01) |
| A61B 1/04 | (2006.01) |
| A61B 1/06 | (2006.01) |

(52) U.S. Cl.
CPC . *A61B 8/12* (2013.01); *A61B 1/05* (2013.01); *A61B 8/445* (2013.01); *A61B 8/4444* (2013.01); *A61B 1/018* (2013.01); *A61B 1/04* (2013.01); *A61B 1/06* (2013.01)

(58) Field of Classification Search
CPC ......... A61B 8/12; A61B 1/05; A61B 8/4444
See application file for complete search history.

(56) References Cited

U.S. PATENT DOCUMENTS

| | | | |
|---|---|---|---|
| 5,226,422 A | 7/1993 | McKeighen et al. | |
| 2013/0072801 A1 | 3/2013 | Hiraoka | |

FOREIGN PATENT DOCUMENTS

| | | | |
|---|---|---|---|
| JP | H11-276422 A | 10/1999 | |
| JP | 2002-113005 A | 4/2002 | |
| JP | 2006-166985 A | 6/2006 | |
| JP | 2008-295749 A | 12/2008 | |

(Continued)

OTHER PUBLICATIONS

International Search Report dated Nov. 18, 2014 issued in PCT/JP2014/074226.

(Continued)

*Primary Examiner* — Serkan Akar
(74) *Attorney, Agent, or Firm* — Scully, Scott, Murphy & Presser, P.C.

(57) ABSTRACT

An ultrasound endoscope distal end portion includes an ultrasound transducer provided at a distal end of an insertion portion, a wiring substrate electrically connected to the ultrasound transducer, a plurality of wires connected to the wiring substrate, a restricting section arranged so as to cover the wiring substrate, wiring substrate side fitting sections provided in the wiring substrate, a first restricting section side fitting section that is provided in the restricting section and fits with the wiring substrate side fitting sections.

7 Claims, 11 Drawing Sheets

(56) References Cited

FOREIGN PATENT DOCUMENTS

| | | |
|---|---|---|
| JP | 2013-184064 A | 9/2013 |
| WO | WO 2007/145182 A1 | 12/2007 |
| WO | WO 2012/157354 A1 | 11/2012 |

OTHER PUBLICATIONS

Japanese Office Action dated Aug. 4, 2015 issued in JP 2015-524538.

ULTRASOUND ENDOSCOPE DISTAL END PORTION TO ACCOMMODATE BEND WIRES AND WIRING SUBSTRATE

CROSS REFERENCE TO RELATED APPLICATION

This application is a continuation application of PCT/JP2014/074226 filed on Sep. 12, 2014 and claims benefit of Japanese Application No. 2013-212693 filed in Japan on Oct. 10, 2013, the entire contents of which are incorporated herein by this reference.

BACKGROUND OF THE INVENTION

1. Field of the Invention

The present invention relates to an ultrasound endoscope distal end portion disposed at a distal end of an insertion portion of an ultrasound endoscope.

2. Description of the Related Art

Ultrasound diagnosis which irradiates a subject with ultrasound, images and diagnoses a state of a body interior from an echo signal is becoming widespread. One of diagnostic apparatuses used for such ultrasound diagnosis is an ultrasound endoscope system.

An ultrasound endoscope of the ultrasound endoscope system includes an ultrasound transducer unit disposed at a distal end portion of an insertion portion which is inserted into the body. The ultrasound transducer unit has a function of converting an electrical signal to ultrasound, transmitting the ultrasound into the body, receiving the ultrasound reflected in the body and converting the ultrasound to an electrical signal.

For example, Japanese Patent Application Laid-Open Publication No. 2006-166985 discloses an ultrasound probe for diagnosis in a body cavity which is inserted into a body cavity and in order to reduce the diameter of a distal end uses a technique of reducing harmful effects caused by using a wiring cable. The conventional ultrasound probe for diagnosis in a body cavity is disclosed as an ultrasound endoscope provided with a convex ultrasound transducer and an image pickup apparatus.

SUMMARY OF THE INVENTION

An ultrasound endoscope distal end portion according to an aspect of the present invention includes: an ultrasound transducer that is provided at a distal end of an insertion portion and has an ultrasound transmission/reception surface that transmits/receives ultrasound and a back surface positioned on a side opposite to the ultrasound transmission/reception surface; a wiring substrate that is arranged on the back surface and is electrically connected to the ultrasound transducer; a plurality of wires that include a bending portion that is connected to the wiring substrate from an upward direction which is a direction toward the ultrasound transmission/reception surface viewed from the wiring substrate to a backward direction which is a direction opposite to the upward direction and thereafter bent toward a direction different from an insertion axis which is a direction in which the insertion portion is inserted; a restricting section that is disposed so as to cover the wiring substrate and is made of a non-conductive material; a wiring substrate side fitting section that is provided on the wiring substrate and fits with the restricting section; and a first restricting section side fitting section that is provided in the restricting section and fits with the wiring substrate.

According to the above-described present invention, it is possible to provide an ultrasound endoscope distal end portion that improves the degree of freedom in an arrangement of components for various functions, can thereby downsize the components, prevent stress from occurring on the wiring connection section to which wires for driving a plurality of ultrasound elements are connected and improve resistance.

DETAILED DESCRIPTION OF THE PREFERRED EMBODIMENTS

Hereinafter, the present invention will be described with reference to the accompanying drawings.

Note that in the following description, drawings based on the following embodiment are schematic drawings and a relationship between a thickness and a width of each component and a ratio of thickness among the respective components or the like are different from those of the actual components, and a dimensional relationship and ratio may differ among the drawings.

Figure 1:
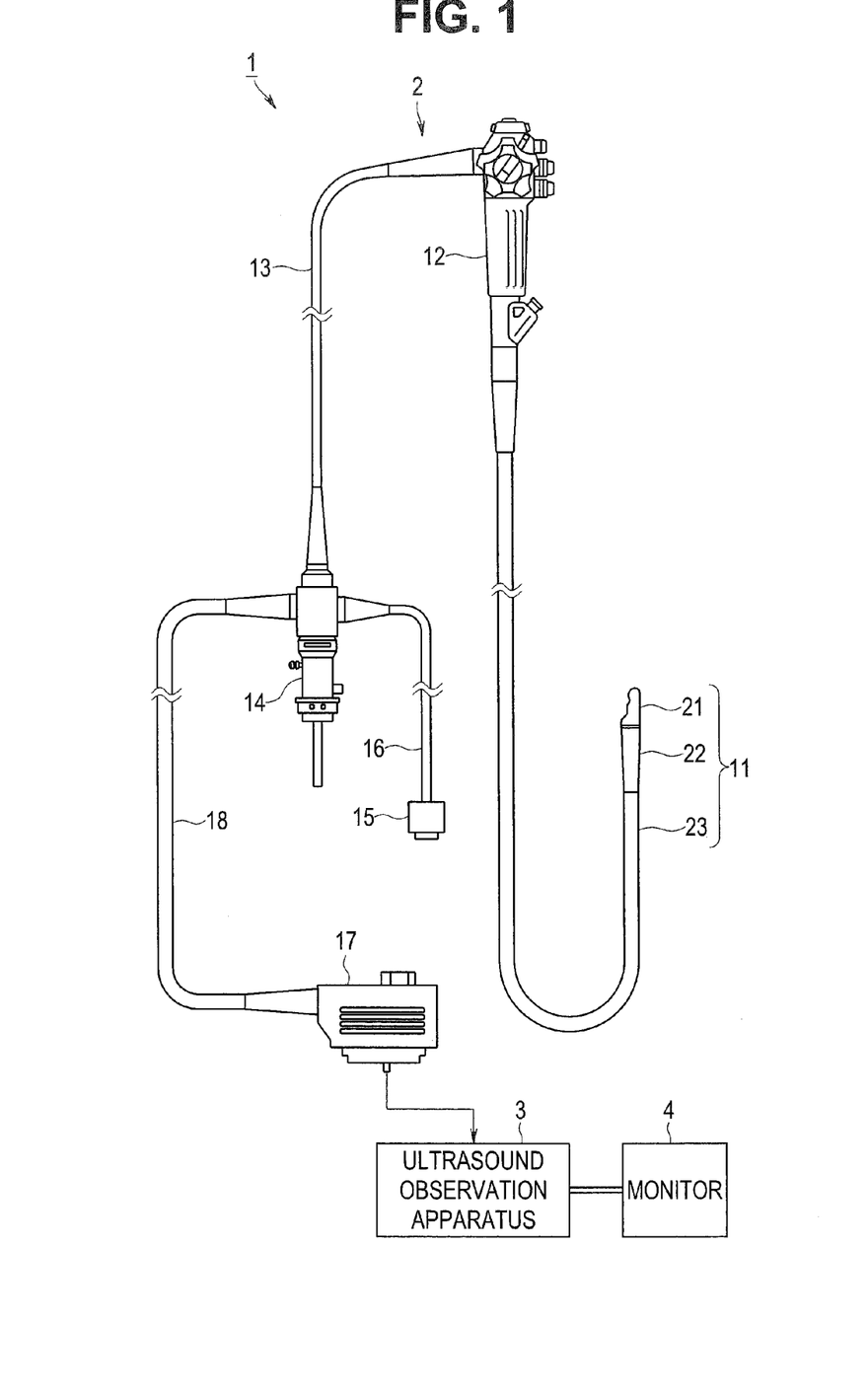
FIG. 1 is a plan view illustrating an overall configuration of an ultrasound endoscope according to an aspect of the present invention.
Figure 2:
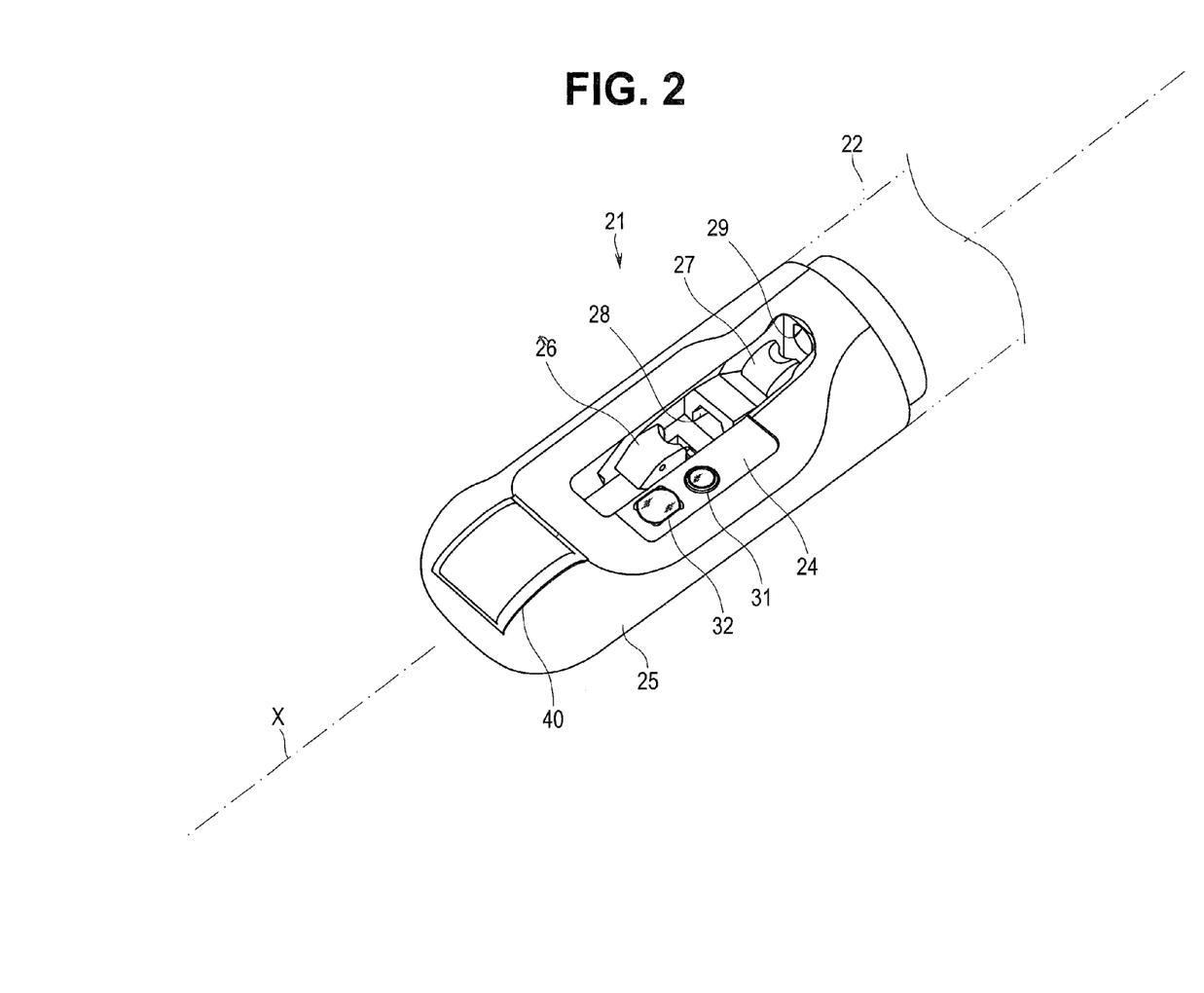
FIG. 2 is a perspective view illustrating a configuration of an ultrasound endoscope distal end portion according to the aspect of the present invention.
Figure 3:
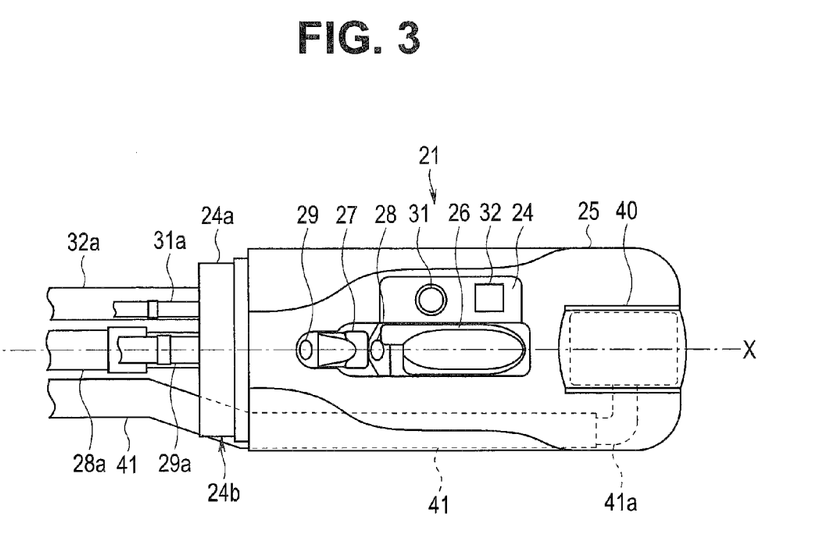
FIG. 3 is a top view illustrating the configuration of the ultrasound endoscope distal end portion according to the aspect of the present invention.
Figure 4:
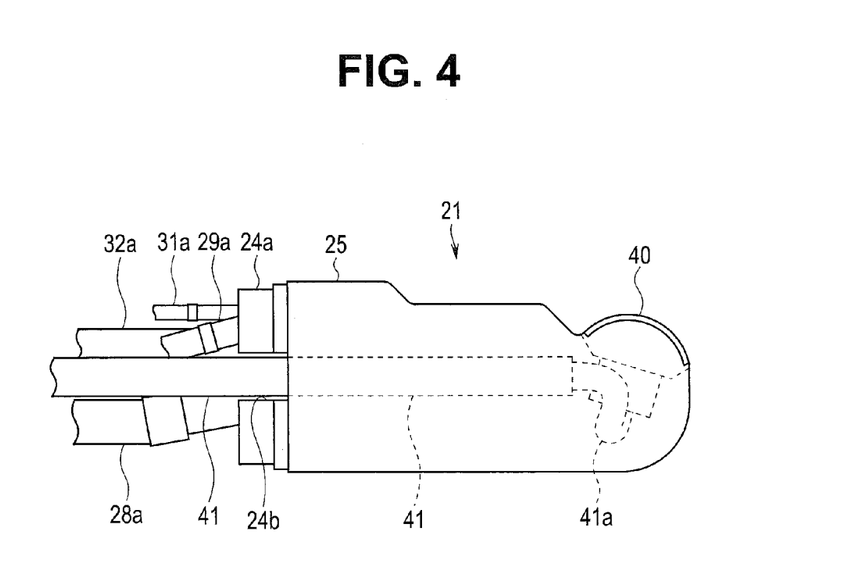
FIG. 4 is a side view illustrating the configuration of the ultrasound endoscope distal end portion according to the aspect of the present invention.
Figure 5:
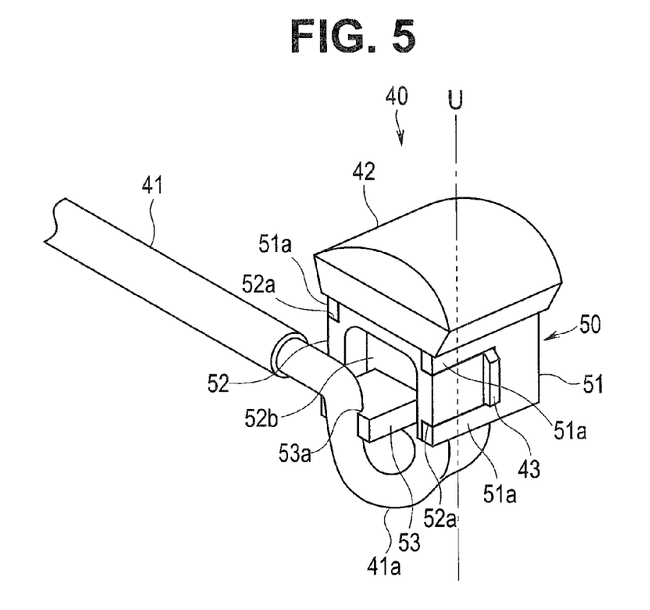
FIG. 5 is a perspective view illustrating a configuration of an ultrasound transducer unit according to the aspect of the present invention.
Figure 6:
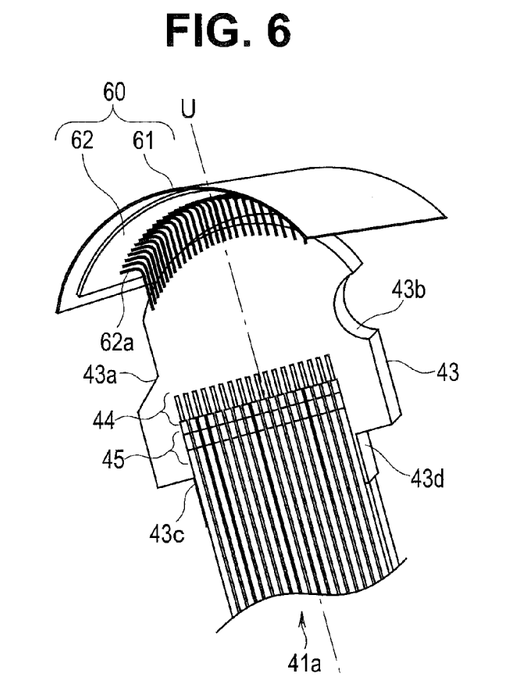
FIG. 6 is a perspective view illustrating a configuration of an ultrasound transducer section and a wiring substrate provided in the ultrasound transducer unit according to the aspect of the present invention.
Figure 7:
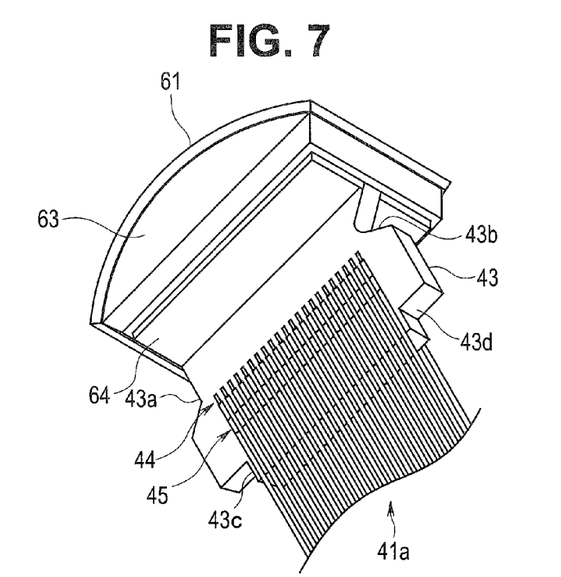
FIG. 7 is a perspective view illustrating a configuration in which the ultrasound transducer section is provided with a backing member holding frame and a backing member in which part of the wiring substrate is embedded according to the aspect of the present invention.
Figure 8:
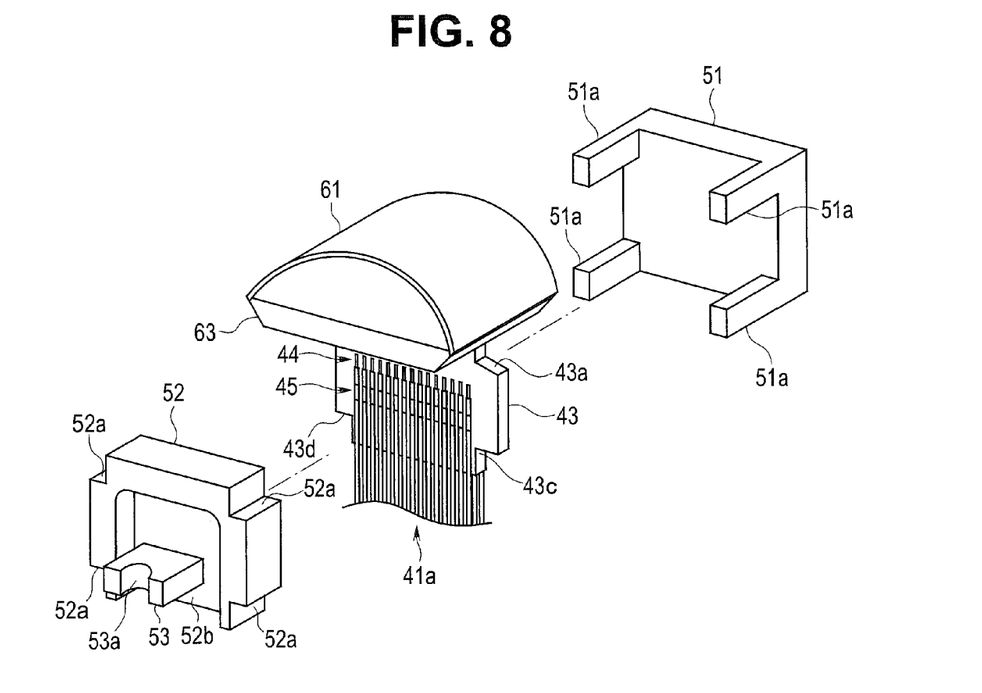
FIG. 8 is an exploded perspective view illustrating a configuration in which wiring holders are disposed so as to sandwich the wiring substrate according to the aspect of the present invention.
Figure 9:
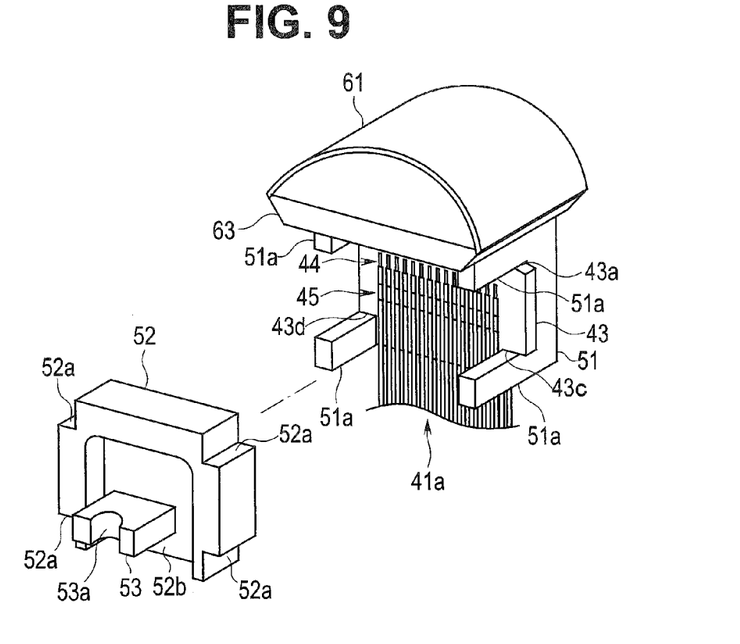
FIG. 9 is an exploded perspective view illustrating a state in which the wiring substrate fits with the first wiring holder according to the aspect of the present invention.
Figure 10:
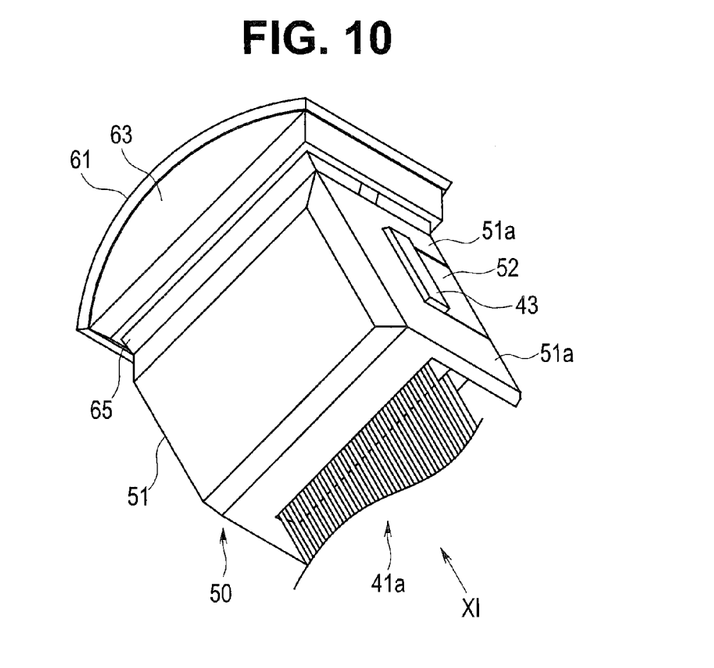
FIG. 10 is a perspective view illustrating a configuration in which an adhesive is provided to fix the backing member holding frame and the wiring holder so as to cover the backing member according to the aspect of the present invention.
Figure 11:
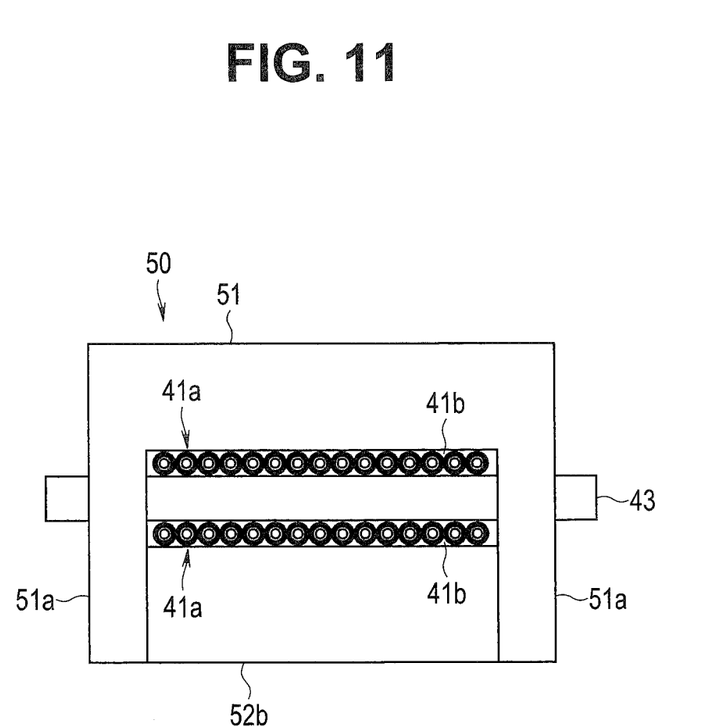
FIG. 11 is an arrow view viewed from the arrow X1 direction in FIG. 10 according to the aspect of the present invention.
Figure 12:
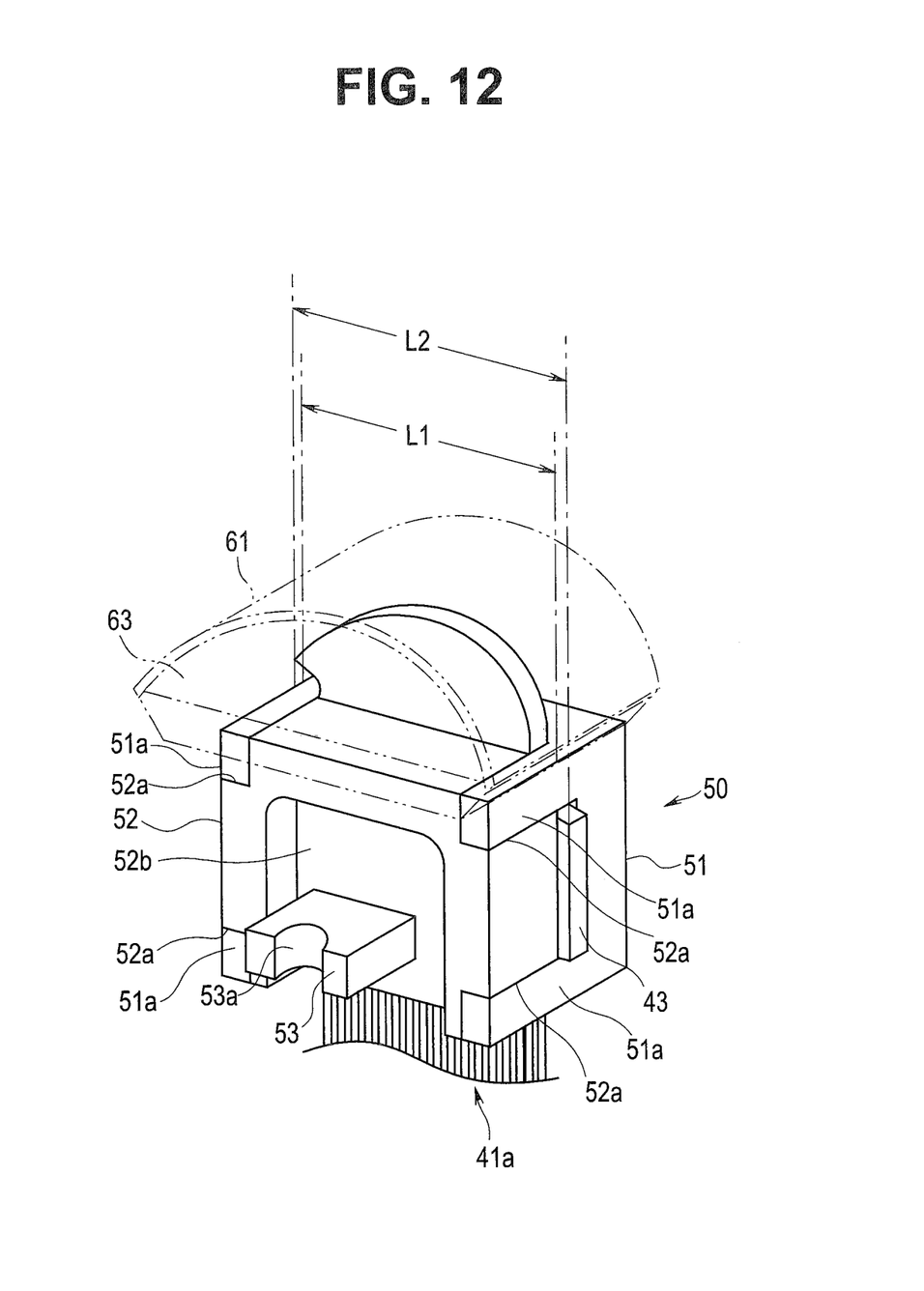
FIG. 12 is a perspective view illustrating a configuration in which the wiring holders are provided so as to sandwich the wiring substrate according to the aspect of the present invention.
Figure 13:
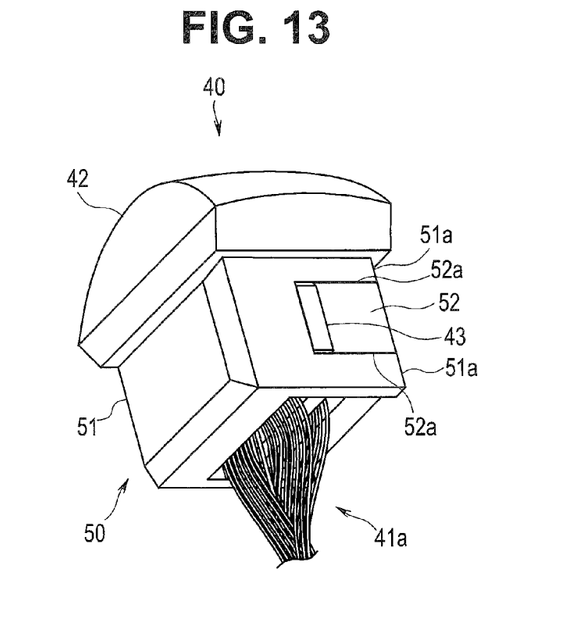
FIG. 13 is a perspective view illustrating a configuration of the ultrasound transducer unit provided with an acoustic lens according to the aspect of the present invention.
Figure 14:
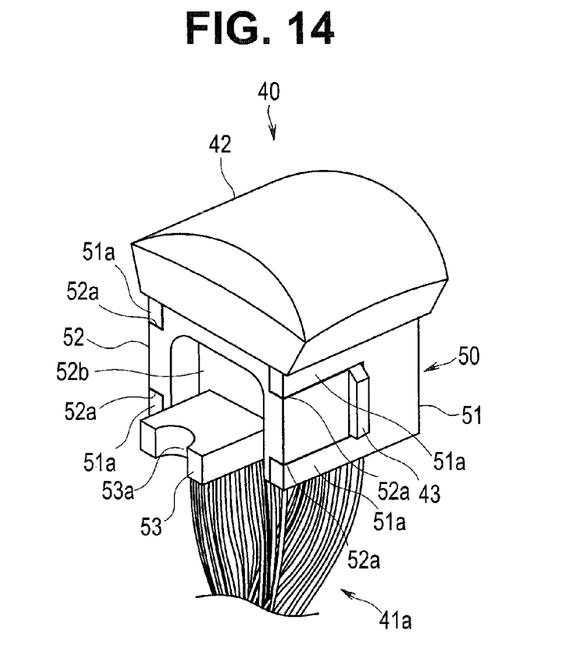
FIG. 14 is a perspective view illustrating a configuration of the ultrasound transducer unit provided with the acoustic lens and viewed from an angle different from that in FIG. 13 according to the aspect of the present invention.
Figure 15:
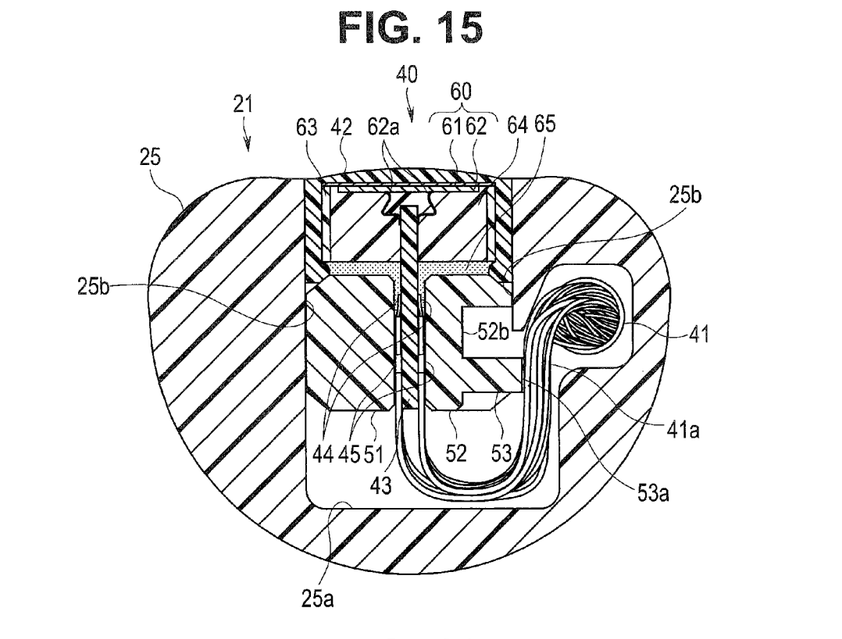
FIG. 15 is a cross-sectional view illustrating a state in which the ultrasound transducer unit is attached to a distal end cover according to the aspect of the present invention.
Figure 16:
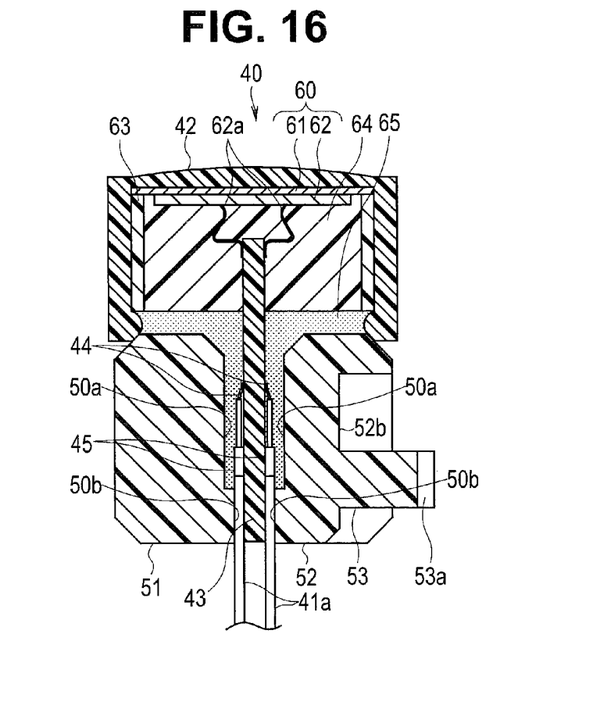
FIG. 16 is a cross-sectional view illustrating a configuration of wiring holders according to a first modification of the aspect of the present invention.
Figure 17:
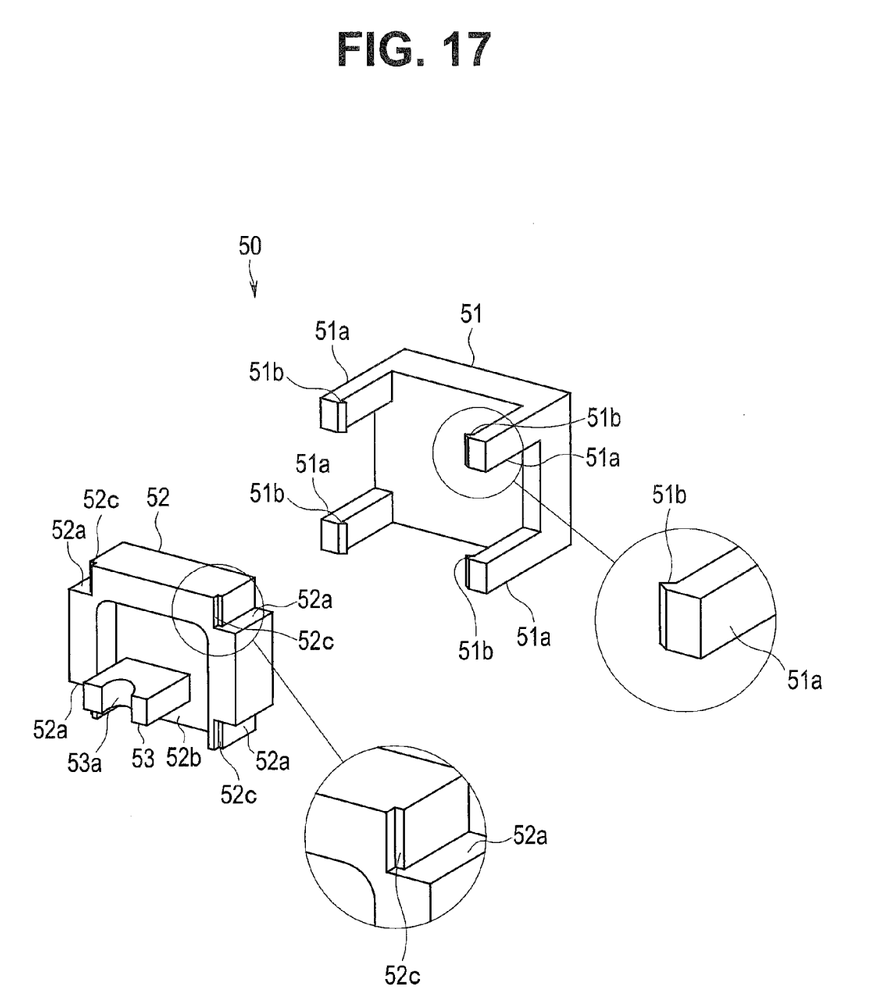
FIG. 17 is an exploded perspective view illustrating a configuration of wiring holders according to a second modification of the aspect of the present invention.

First, the present invention will be described using FIG. 1 to FIG. 16. Note that FIG. 1 to FIG. 16 are related to an embodiment of an aspect of the present invention: FIG. 1 is a plan view illustrating an overall configuration of an ultrasound endoscope, FIG. 2 is a perspective view illustrating a configuration of an ultrasound endoscope distal end portion, FIG. 3 is a top view illustrating the configuration of the ultrasound endoscope distal end portion, FIG. 4 is a side view illustrating the configuration of the ultrasound endoscope distal end portion, FIG. 5 is a perspective view illustrating a configuration of an ultrasound transducer unit, FIG. 6 is a perspective view illustrating a configuration of an ultrasound transducer section and a wiring substrate provided in the ultrasound transducer unit, FIG. 7 is a perspective view illustrating a configuration in which the ultrasound transducer section is provided with a backing member holding frame and a backing member in which part of the wiring substrate is embedded, FIG. 8 is an exploded perspective view illustrating a configuration in which wiring holders are disposed so as to sandwich the wiring substrate, FIG. 9 is an exploded perspective view illustrating a state in which the wiring substrate fits with the first wiring holder, FIG. 10 is a perspective view illustrating a configuration in which an adhesive is provided to fix the backing member holding frame and the wiring holder so as to cover the backing member, FIG. 11 is an arrow view viewed from the arrow X1 direction in FIG. 10, FIG. 12 is a perspective view illustrating a configuration in which the wiring holders are provided so as to sandwich the wiring substrate, FIG. 13 is a perspective view illustrating a configuration of the ultrasound transducer unit provided with an acoustic lens, FIG. 14 is a perspective view illustrating a configuration of the ultrasound transducer unit provided with the acoustic lens and viewed from an angle different from that in FIG. 13, FIG. 15 is a cross-sectional view illustrating a state in which the ultrasound transducer unit is attached to a distal end cover, FIG. 16 is a cross-sectional view illustrating a configuration of wiring holders according to a first modification and FIG. 17 is an exploded perspective view illustrating a configuration of wiring holders according to a second modification.

As shown in FIG. 1, an ultrasound endoscope system 1 is configured by mainly including an ultrasound endoscope 2, an ultrasound observation apparatus 3 and a monitor 4. The ultrasound endoscope 2 is provided with an elongated insertion portion 11 which is inserted into the body, an operation portion 12 disposed at a proximal end of the insertion portion 11 and a universal cord 13 that extends from the operation portion 12.

A light source connector 14 connected to a light source apparatus (not shown) is disposed at a proximal end portion of the universal cord 13. A cable 16 connected to a camera control unit (not shown) via an electrical connector 15 and a cable 18 connected to the ultrasound observation apparatus 3 via an ultrasound connector 17 extend from the light source connector 14. Note that the monitor 4 that displays ultrasound images is connected to the ultrasound observation apparatus 3.

The insertion portion 11 is configured by consecutively connecting, in order from the distal end side, a distal end constituting portion (hereinafter referred to as "distal end portion") 21 as an ultrasound endoscope distal end portion, a bending portion 22 located at a back end of the distal end portion 21, a flexible tube 23 which is thin, long and flexible, located at a back end of the bending portion 22 and extending to the operation portion 12.

Note that since other components of the ultrasound endoscope 2 are well known, detailed description of those components will be omitted.

Next, the configuration of the ultrasound endoscope distal end portion (hereinafter simply referred to as "distal end portion") 21 of the present embodiment will be described in detail below.

As shown in FIG. 2, the distal end portion 21 of the ultrasound endoscope 2 is made up of a metallic distal end rigid portion 24 cladded with a synthetic resin distal end cover 25. An ultrasound transducer unit 40 is disposed on one surface of the distal end portion 21 which is a top surface of the distal end cover 25 orthogonal to an insertion axis X of the insertion portion 11, as an ultrasound transducer provided with a plurality of (here two) first and second raising stands 26 and 27, a plurality of (here two) first and second channel opening portions 28 and 29, an optical observation window 31, an optical illuminating window 32 and a plurality of ultrasound elements.

Note that the ultrasound transducer unit 40 here is of a convex scanning type in which a plurality of ultrasound elements are arranged in a convex bent shape.

Furthermore, the distal end portion 21 is provided with the ultrasound transducer unit 40, the first raising stand 26, the first channel opening portion 28, the second raising stand 27 and the second channel opening portion 29, arranged side by side in order from the distal end along the insertion axis X.

That is, in the distal end portion 21 of the present embodiment, the ultrasound transducer unit 40 is provided on the distal end side and the first raising stand 26, the first channel opening portion 28, the second raising stand 27 and the second channel opening portion 29 are arranged side by side on a straight line along the insertion axis X on the proximal end.

Note that the first raising stand 26 and the second raising stand 27 are provided so as to be freely rotatable in a concave portion formed in the distal end rigid portion 24 of the distal end portion 21.

The first raising stand 26 and the second raising stand 27 are operated to rotate through operation of a raising lever (not shown) provided on the operation portion 12. A detailed configuration in which the first raising stand 26 and the second raising stand 27 rise and fall is the same as the conventional one, and so description thereof is omitted.

The first raising stand 26 or the second raising stand 27 is operated to rotate in the raising direction, and can thereby raise/lead out a treatment instrument such as a contrast imaging tube or a puncture needle projecting from the first channel opening portion 28 or the second channel opening portion 29 in a direction orthogonal to the insertion axis X.

Note that the first channel opening portion 28 and the second channel opening portion 29 constitute openings on the distal end side of two treatment instrument channels (not shown) disposed from the distal end portion 21 to the insertion portion 11 and the operation portion 12. The two treatment instrument channels are connected to a treatment instrument insertion port (not shown) provided in the operation portion 12 and a treatment instrument is introduced from the treatment instrument insertion port.

The optical observation window 31 here constitutes an optical observation system with respect to an image pickup unit (not shown) provided with a solid image pickup device as image pickup means disposed in the distal end portion 21. That is, the image pickup unit incorporated in the distal end portion 21 is disposed on the back side of the optical observation window 31.

Light of a subject image from a direction orthogonal to the insertion axis X is incident on the optical observation window 31 and the incident light is photoelectrically converted by the image pickup unit. Note that the image pickup means of the ultrasound endoscope 2 is not limited to the image pickup unit, but may also have a configuration using an image guide.

An end face of a light guide bundle (not shown) for transmitting illuminating light from the light source apparatus (not shown), which is inserted and arranged through the distal end portion 21, the insertion portion 11, the operation portion 12 and the universal cord 13, is provided so as to face the back (reverse) side of the optical illuminating window 32. That is, the optical illuminating window 32 constitutes an illumination optical system that irradiates the subject with the illuminating light radiated from the end face of the light guide bundle provided in the distal end portion 21.

Note that illumination means of the ultrasound endoscope 2 is not limited to the light guide that transmits the illuminating light from the light source apparatus, but may also have a configuration using illumination means such as LED illumination.

As described above, the ultrasound endoscope 2 of the present embodiment adopts a configuration in which the ultrasound transducer unit 40 is arranged at the distal end of the distal end portion 21 of the insertion portion 11, and the first raising stand 26, the first channel opening portion 28, the second raising stand 27 and the second channel opening portion 29 are linearly arranged side by side in order on the hand side, which is the proximal end side on the insertion axis X as the central axis of the distal end portion 21, so as to improve operability of treatment using a treatment instrument such as a contrast imaging tube or a puncture needle under an ultrasound image guide by the ultrasound transducer unit 40.

In such a configuration, the ultrasound endoscope 2 provides the respective centers of the first raising stand 26, the first channel opening portion 28, the second raising stand 27 and the second channel opening portion 29 on a plane substantially identical to an ultrasound scanning plane under the ultrasound image guide by the ultrasound transducer unit 40, thereby causes a treatment instrument such as a contrast imaging tube or a puncture needle led out from the first channel opening portion 28 or the second channel opening portion 29 to rise toward the ultrasound scanning plane by the first raising stand 26 or the second raising stand 27 to ensure that the treatment instrument is reflected under the ultrasound image.

Note that in the configuration of the distal end portion 21 in the present embodiment, as shown in FIG. 3 and FIG. 4, an ultrasound cable 41 extends backward from the ultrasound transducer unit 40 provided at the distal end.

More specifically, the ultrasound cable 41 constitutes a drive cable that drives the ultrasound transducer unit 40 and includes a bending portion where an ultrasound cable wire bundle 41a extends from below the ultrasound transducer unit 40 inside the distal end cover 25, is bent toward one side of the ultrasound transducer unit 40, and then further bent backward. Furthermore, the ultrasound cable 41 is configured by covering the ultrasound cable wire bundle 41a, which is bent and extends backward, with an external coat.

The ultrasound cable 41 is inserted through the insertion portion 11, the operation portion 12, the universal cord 13, the light source connector 14 and the cable 18, and extends to the ultrasound connector 17 connected to the ultrasound observation apparatus 3.

The ultrasound cable 41 configured in this way is offset toward one side from the center of the ultrasound transducer unit 40 and extends from the back end of the edge portion of the distal end cover 25 directly into the bending portion 22 of the insertion portion 11.

To be more specific, the ultrasound cable 41 is not inserted into the distal end rigid portion 24 covered with the distal end cover 25 in the distal end portion 21 but is inserted through one side of the distal end cover 25.

The ultrasound cable 41 is placed in a notch 24b formed on one side of a proximal end connection portion 24a of the distal end rigid portion 24, is bent toward the center direction (inner diameter direction) of the insertion portion 11 via the notch 24b and inserted into the bending portion 22.

That is, the ultrasound cable 41 extends along one side in the distal end cover 25 in the distal end portion 21, is then inserted into the bending portion 22 from the notch 24b of the proximal end connection portion 24a provided at the back end of the distal end rigid portion 24 and placed in the insertion portion 11. Note that a bending piece (not shown) at the distalmost end of the bending portion 22 is connected to the proximal end connection portion 24a of the distal end rigid portion 24.

By adopting such a configuration, even when two treatment instrument channels 28a and 29a connected in the distal end rigid portion 24 so as to communicate with the first channel opening portion 28 and the second channel opening portion 29 provided in the distal end portion 21 are provided on a plane substantially identical to the ultrasound scanning plane of the ultrasound transducer unit 40, the ultrasound cable 41 need not be provided on the plane substantially identical to the ultrasound scanning plane, thus making it possible to reduce the size of the distal end portion 21.

In addition, the ultrasound cable 41 of the distal end portion 21 is offset toward the one side direction from the center of the ultrasound transducer unit 40, inserted at a position deviated from the insertion axis X and not provided on the plane substantially identical to the ultrasound scanning plane of the ultrasound transducer unit 40.

For this reason, in the distal end portion 21, there are fewer restrictions of the arrangement of the ultrasound cable 41 in the space to arrange various components such as a plurality of operation wires (not shown) for operating to raise the first raising stand 26 or the second raising stand 27 disposed inside, an image pickup cable 31a that extends from an image pickup unit (not shown) and a light guide bundle 32a that extends to the optical illuminating window 32, and it is therefore possible to improve the degree of freedom of layout of the various components for a size reduction.

Here, a more specific configuration of the ultrasound transducer unit 40 provided at the distal end portion 21 of the present embodiment will be described in detail below. Note that known configurations will be described only briefly below.

When the ultrasound transducer unit 40 is mounted in the distal end portion 21 as shown in FIG. 5, a resin, e.g., non-conductive silicone resin acoustic lens 42 is molded into a convex shape as an exposed portion.

Furthermore, the ultrasound transducer unit 40 includes a non-conductive wiring holder 50 made up of a first wiring holder 51 and a second wiring holder 52 that fixes a wiring substrate 43 so as to cover both sides thereof and cover a wiring connection portion and a ground connection portion, which will be described later, of the wiring substrate 43 to which a plurality of wires of the ultrasound cable wire bundle 41a of the ultrasound cable 41 are connected, as a restricting section that fits with and restricts the wiring substrate 43 so as not to move. Note that the configuration of the wiring holder 50 will be described later in detail.

In the wiring substrate 43 disposed inside the ultrasound transducer unit 40, the respective wires of the ultrasound cable wire bundle 41a are connected side by side in a direction substantially orthogonal to a transducer sound axis U so as to extend toward one side which is a downward side where the wires become non-parallel to each other as shown in FIG. 6. Note that the respective wires of the ultrasound cable wire bundle 41a are coaxial cables and are connected to both sides of the wiring substrate 43.

More specifically, the wiring substrate 43 includes a wiring connection portion 44 formed with inner conductors of the respective coaxial cables of the ultrasound cable wire bundle 41a connected by solder and a ground connection portion 45 formed with outer conductors of the respective coaxial cables connected by solder, and a plurality of connection lands (not shown) are formed in the wiring connection portion 44 and the ground connection portion 45.

As described above, the wiring connection portion 44 and the ground connection portion 45 are arranged side by side toward a direction substantially orthogonal to the transducer sound axis U along the plane of the wiring substrate 43. Note that the wiring connection portion 44 and the ground connection portion 45 are provided on both sides of the wiring substrate 43.

That is, the plurality of coaxial cables of the ultrasound cable wire bundle 41a are connected at the wiring connection portion 44 and the ground connection portion 45 so as to be arranged side by side in the direction substantially orthogonal to the transducer sound axis U along the plane of the wiring substrate 43 on both sides of the wiring substrate 43.

Thus, the length of the wiring substrate 43 in the direction along the transducer sound axis U can be reduced. As a result, it is possible to reduce the size of the wiring substrate 43 and reduce the size of the ultrasound transducer unit 40 accordingly.

The wiring substrate 43 is provided with four concave portions 43a, 43b, 43c and 43d which become a wiring substrate side fitting portion which is formed by cutting out both sides on the upper side halfway and two corners on the lower side as the configuration for positioning when the wiring substrate 43 is fixed to the above-described wiring holder 50. The roles of the four concave portions 43a, 43b, 43c and 43d will be described later.

Furthermore, the wiring substrate 43 is provided with a wiring group 62a in an arc-shaped upper edge portion formed on the top side. The wiring group 62a is electrically connected to a plurality of connection lands and wiring patterns of the wiring connection portion 44 and the ground connection portion 45 to which the respective coaxial cables of the ultrasound cable wire bundle 41a are connected and is a plurality of wires connected to respective piezoelectric elements of a piezoelectric element array 62.

Note that the piezoelectric element array 62 is provided on the back (reverse) side of a tabular acoustic matching layer 61 having an arc-shaped cross section. The acoustic matching layer 61 and the piezoelectric element array 62 constitute an ultrasound transducer section 60. Furthermore, the surface of the acoustic matching layer 61 constitutes an ultrasound transmission/reception surface to transmit/receive ultrasound.

A backing member holding frame 63 which is a tabular frame body disposed so as to surround the acoustic matching layer 61 along the edge portion thereof on the back (reverse) side on which the piezoelectric element array 62 is provided as shown in FIG. 7 is fixed to the acoustic matching layer 61 using an adhesive. A backing member 64 made of a non-conductive member is provided in the space formed of the back (reverse) side of the acoustic matching layer 61 and the backing member holding frame 63.

The backing member 64 is arranged by covering part of the wiring substrate 43 from the top to a halfway position, the piezoelectric element array 62 and the wiring group 62a extending from the wiring substrate 43 connected to the piezoelectric element array so as to embed these parts, and the entire side face thereof is held by the backing member holding frame 63.

Thus, the first wiring holder 51 and the second wiring holder 52 of the aforementioned non-conductive wiring holder 50 fit with the wiring substrate 43 to which the ultrasound transducer section 60 is fixed via the backing member 64 so as to sandwich both sides of the portion of the wiring substrate 43 below the portion thereof embedded in the backing member 64 as shown in FIG. 8 to FIG. 10.

The first wiring holder 51 and the second wiring holder 52 fit with each other and are fixed so as to sandwich the wiring substrate 43 from both sides in such a way as to cover the wiring connection portion 44 and the ground connection portion 45 to which the plurality of coaxial cables of the ultrasound cable wire bundle 41a are connected, which are respectively provided linearly on both sides of the wiring substrate 43.

Note that a non-conductive plastic material, a ceramic material, or a material including a metal coated with a non-conductive coat or the like is used for both the first wiring holder 51 and the second wiring holder 52 of the wiring holder 50.

The configuration of the wiring holder 50 will be described in detail below.

The first wiring holder 51 of the wiring holder 50 has four fitting protruding portions 51a as first restricting section side fitting portions that extend from the four corners of the plane opposite to one plane of the wiring substrate 43.

When the wiring substrate 43 fits with the first wiring holder 51, each of the four fitting protruding portions 51a fits with one of the four concave portions 43a, 43b, 43c and 43d as the wiring substrate side fitting portion of the wiring substrate 43 located at the corresponding position as shown in FIG. 9.

Thus, the wiring substrate 43 is located at a predetermined position of the first wiring holder 51 held by the four fitting protruding portions 51a. That is, the wiring substrate 43 is restricted so as not to move at a predetermined position of the first wiring holder 51.

The second wiring holder 52 of the wiring holder 50 has four fitting concave portions 52a as second restricting member side fitting portions formed by being cut out in the four corners and a concave portion 52b is formed on the side opposite to the plane facing one plane of the wiring substrate 43.

A cable holding portion 53 as a wiring holding portion that holds the ultrasound cable wire bundle 41a protrudes from the concave portion 52b. Note that an arc-shaped concave portion 53a is formed in an end face on the protruding side of the cable holding portion 53.

In the wiring holder 50 configured as described above, the wiring substrate 43 fits with the first wiring holder 51 first. At this time, as described above, each of the four fitting protruding portions 51a of the first wiring holder 51 fits with one of the four concave portions 43a, 43b, 43c and 43d of the wiring substrate 43 located at the corresponding positions, the wiring substrate 43 is positioned to and fitted with the first wiring holder 51 and restricted so as not to move.

Note that the wiring substrate 43 is pushed in along and fits with the four fitting protruding portions 51a until a position where the wiring substrate 43 comes into contact with the first wiring holder 51.

Next, the second wiring holder 52 is moved toward the other plane of the wiring substrate 43 which is fitted with the first wiring holder 51 and is fitted so as to face the first wiring holder 51 side.

Note that the second wiring holder 52 is fitted with the first wiring holder 51 so that the plane opposite to the plane on which the concave portion 52b and the cable holding portion 53 are provided faces the wiring substrate 43.

Each of the four fitting protruding portions 51a of the first wiring holder 51 fits with one of the four fitting concave portions 52a of the second wiring holder 52 located at the corresponding positions. Thus, the second wiring holder 52 is positioned to and fitted with the first wiring holder 51.

The wiring holder 50 is pushed in along the four fitting protruding portions 51a up to a position at which the second wiring holder 52 comes into contact with the wiring substrate 43 and comes into fitting as shown in FIG. 10 and FIG. 11. Note that with the wiring substrate 43 sandwiched between the first wiring holder 51 and the second wiring holder 52, the first wiring holder 51 and the second wiring holder 52 including the wiring substrate 43 are fixed to each other using an adhesive 41b.

The wiring substrate 43 sandwiched by the wiring holder 50 in this way is restricted so as not to move in the wiring holder 50, the adhesive flows in around the wiring connection portion 44 and the ground connection portion 45 of the wiring substrate 43 disposed on both sides thereof, filling gaps, and the inside thereof is sealed with the contacting surface of the first wiring holder 51 or the second wiring holder 52 and the adhesive 41b which is the fixing section.

Thus, the wiring connection portion 44 and the ground connection portion 45 of the wiring substrate 43 are completely covered with the non-conductive wiring holder 50 which is fixed by the adhesive as the fixing section, and electrical insulating properties thereof are kept.

Furthermore, an adhesive 65 as a fixing section is also embedded and fixed in gaps between the top edge portion of the wiring holder 50 and the backing member 64, and the backing member holding frame 63 and the wiring holder 50 are bonded and fixed together.

Note that the wiring holder 50 may be bonded and fixed to either the backing member holding frame 63 or the backing member 64, but the wiring holder 50 is preferably bonded and fixed to both the backing member holding frame 63 and the backing member 64.

The reason is that when the wiring holder 50 is bonded to both the backing member holding frame 63 and the backing member 64, the wiring substrate 43 is firmly fixed to the piezoelectric element array 62 without operating, providing an advantage of being able to prevent trouble from occurring by wire breakage caused by deformation of the wiring group 62a connected to each piezoelectric element.

A maximum length (width) L1 of the wiring holder 50 when the first wiring holder 51 and the second wiring holder 52 fit with each other is set to be shorter than a maximum length (width) L2 of the wiring substrate 43 in the width direction as shown in FIG. 11.

Such a configuration makes it possible to cover the wiring substrate and the wiring portion connected to the wiring substrate with the holder having a width smaller than the width of the wiring substrate, and reduce the size of the whole structure while maintaining insulating properties from outside the wiring portion.

Next, the acoustic lens 42 is molded so as to cover the acoustic matching layer 61, the backing member holding frame 63 and the top edge portion of the wiring holder 50, and the ultrasound transducer unit 40 is completed as shown in FIG. 13 and FIG. 14.

Note that with the acoustic matching layer 61 and the backing member holding frame 63 coated with, e.g., a silicone resin in liquid form so as to cover them, the acoustic lens 42 of the ultrasound transducer unit 40 is cast into a mold and molded through thermosetting.

The ultrasound transducer unit 40 configured in this way is mounted on the distal end cover 25 of the distal end portion 21 of the ultrasound endoscope 2.

At this time, the ultrasound cable wire bundle 41a extending from below the ultrasound transducer unit 40 is bent toward the one side direction which is the cable holding portion 53 side provided in the second wiring holder 52 of the wiring holder 50, further bent upward, arranged and held so as to be hooked on the concave portion 53a of the cable holding portion 53 (see FIG. 5).

Furthermore, the ultrasound cable wire bundle 41a held by the concave portion 53a of the cable holding portion 53 is bent backward, and made to extend from the back end of the edge portion of the distal end cover 25 directly into the bending portion 22 of the insertion portion 11 as described above (see FIG. 3 and FIG. 4).

Note that the concave portion 53a of the cable holding portion 53 here is assumed to be arc-shaped, but not being limited to this, the concave portion 53a needs only to be able to hold the ultrasound cable wire bundle 41a and may be shaped like a through hole. Note that when the cable holding portion 53 is provided with a through hole, a plurality of coaxial cables are subjected to cable termination after passing the ultrasound cable wire bundle 41a through the through hole beforehand.

The distal end cover 25 of the distal end portion 21 in which the ultrasound transducer unit 40 is mounted constitutes a housing that holds the ultrasound transducer unit 40 as shown in FIG. 15, forming a unit housing section 25a as a housing side fitting portion formed into a concave portion in which the ultrasound transducer unit 40 is housed and fixed using an adhesive.

The unit housing section 25a includes a side face portion 25b which is set so as to include micro clearances at respective side faces whereby the first wiring holder 51 and the second wiring holder 52 of the wiring holder 50 separate from each other when the ultrasound transducer unit 40 is housed.

That is, when the ultrasound transducer unit 40 is mounted and fixed in the distal end cover 25, the side face of the wiring holder 50 of the ultrasound transducer unit 40 comes into contact with and fits with the side face portion 25b of the unit housing section 25a, thus restricting the ultrasound transducer unit 40 so as not to tilt.

This ensures the ultrasound transducer unit 40 to be mounted in the distal end cover 25 in a designed predetermined direction without tilting. Note that a free space of the unit housing section 25a produced when the ultrasound transducer unit 40 is fixed to the distal end cover 25 is filled with resin such as an adhesive to keep airtightness.

In this way, the ultrasound transducer unit 40 is positioned with the side face of the wiring holder 50 contacting the side face portion 25b of the unit housing section 25a of the distal end cover 25, fixed using an adhesive to prevent postural sway, and further firmly fixed with the free space of the unit housing section 25a also filled with resin. This allows the ultrasound transducer unit 40 to be accurately fixed to the distal end cover 25 which serves as a housing.

As described above, the distal end portion 21 of the ultrasound endoscope 2 of the present embodiment is completely covered and electrical insulation is ensured by sandwiching and fixing the wiring substrate 43 of the ultrasound transducer unit 40 between the first wiring holder 51 or the second wiring holder 52 of the wiring holder 50, and sealing the wiring connection portion 44 and the ground connection portion 45 of the wiring substrate 43 with an adhesive.

The first wiring holder 51 and the second wiring holder 52 of the wiring holder 50 sandwich and fix also the connection end portions of the plurality of wires of the ultrasound cable wire bundle 41a connected to the wiring connection portion 44 and the ground connection portion 45 of the wiring substrate 43 together with the wiring substrate 43, and therefore provides a configuration preventing wire breakage of the wiring connection portion 44 and the ground connection portion 45 of the wiring substrate 43 to which the plurality of wires of the ultrasound cable wire bundle 41a are connected even when the plurality of wires of the ultrasound cable wire bundle 41a extending from below the wiring holder 50 is bent and stress is produced.

That is, when the ultrasound transducer unit 40 of the present embodiment is mounted in the distal end cover 25 of the distal end portion 21, as described above, the ultrasound cable wire bundle 41a extending from below the wiring holder 50 is first bent toward the side of the wiring holder 50, then bent upward and bent backward.

Therefore, although stress is produced in the ultrasound cable wire bundle 41a when bent, the wiring connection portion 44 and the ground connection portion 45 of the wiring substrate 43 to which the ultrasound cable wire bundle 41a is connected are sandwiched and fixed between the first wiring holder 51 and the second wiring holder 52 of the wiring holder 50, thus improving resistance against stress and preventing wire breakage of the wiring connection portion 44 and the ground connection portion 45.

Furthermore, as described above, in the distal end portion 21 of the present embodiment, the ultrasound cable 41 is offset from the center of the ultrasound transducer unit 40 and is not provided on any plane substantially identical to the ultrasound scanning plane of the ultrasound transducer unit 40, and so there are fewer restrictions of the arrangement of the ultrasound cable 41 in the space for arranging various components disposed therein, and it is thereby possible to improve the degree of freedom of layout design of various components for a size reduction.

Note that the following configuration may be used for the wiring holder 50 provided in the ultrasound transducer unit 40 mounted in the distal end portion 21.

First Modification

In the wiring holder 50 here, concave portions 50a are formed in mutually opposed planes whereby the first wiring holder 51 and the second wiring holder 52 sandwich the wiring substrate 43 as shown in FIG. 16.

The concave portions 50a are formed at positions where the wiring connection portion 44 and the ground connection portion 45 of the wiring substrate 43 are accommodated when the wiring substrate 43 is sandwiched, and by filling and thereby sealing the inside of the concave portions 50a with the adhesive 65, it is possible to completely cover the wiring connection portion 44 and the ground connection portion 45 with the adhesive 65 and keep electrical insulating properties.

When sandwiching the wiring substrate 43, the first wiring holder 51 and the second wiring holder 52 sandwich and hold the wiring substrate 43 so as to press the coated portions of the respective coaxial wires of the ultrasound cable wire bundle 41a by respective planes 50b below the concave portions 50a.

The wiring holder 50 of the present modification can reliably fill the wiring connection portion 44 and the ground connection portion 45 with the adhesive 65, thereby secure insulating properties, and sandwich and firmly fix the respective coaxial wires of the wiring substrate 43 and the ultrasound cable wire bundle 41a.

Second Modification

As shown in FIG. 17, the wiring holder 50 here includes the four fitting protruding portions 51a of the first wiring holder 51 respectively provided with inwardly protruding convex portions 51b at their respective protruding ends and the four fitting concave portions 52a of the second wiring holder 52 respectively provided with concave portions 52c that fit with the convex portions 51b of the fitting protruding portions 51a, adopting a so-called snap-fit structure that mechanically fixes the holders.

By adopting such a configuration, the wiring holder 50 has a configuration capable of increasing the fixing strength of the first wiring holder 51 and the second wiring holder 52 and eliminating the need, when bonding and fixing the first wiring holder 51 and the second wiring holder 52, for holding these holders after sandwiching the wiring substrate 43.

Note that although the wiring holder 50 is assumed to be made up of two members: the first wiring holder 51 and the second wiring holder 52, the wiring holder 50 is not limited to this, but the wiring holder 50 may also have a rectangular cylindrical shape if it has a structure that covers the respective coaxial wires of the wiring substrate 43 and the ultrasound cable wire bundle 41a. Furthermore, the wiring holder 50 needs only to have a structure of reliably covering and fixing at least the wiring connection portion 44 and the ground connection portion 45 of the wiring substrate 43.

As described above, the distal end portion 21 as the ultrasound endoscope distal end portion according to the present embodiment can be reduced in size by improving the degree of freedom in arrangements of the components for various functions and can be configured to have improved resistance by preventing stress from occurring on the wiring connection portion 44 and the ground connection portion 45 provided on the wiring substrate 43 to which wires for driving the ultrasound transducer section 60 are connected.

The invention described in the aforementioned embodiments is not limited to the embodiments and modifications, and can be modified in various ways without departing from the spirit and scope of the present invention in an implementation phase. The aforementioned embodiments include inventions in various phases and various inventions can be extracted in appropriate combinations of a plurality of disclosed components.

For example, even when some components are deleted from all the components shown in the embodiments, if it is possible to solve the described problems and obtain the described effects, the configuration with the components deleted can be extracted as an invention.

What is claimed is:

1. An ultrasound endoscope distal end portion comprising:
    an ultrasound transducer that is provided at a distal end of an insertion portion and has an ultrasound transmission/reception surface that transmits/receives ultrasound and a back surface positioned on a side opposite to the ultrasound transmission/reception surface;
    a wiring substrate that is arranged on the back surface and is electrically connected to the ultrasound transducer;
    a plurality of wires that include a bending portion that is connected to the wiring substrate from an upward direction which is a direction toward the ultrasound transmission/reception surface viewed from the wiring substrate to a backward direction which is a direction opposite to the upward direction and thereafter bent toward a direction different from an insertion axis which is a direction in which the insertion portion is inserted;
    a restricting section that is disposed so as to cover the wiring substrate and is made of a non-conductive material;
    a wiring substrate side fitting section that is provided on the wiring substrate and fits with the restricting section; and
    a first restricting section side fitting section that is provided in the restricting section and fits with the wiring substrate.

2. The ultrasound endoscope distal end portion according to claim 1, further comprising:
    a backing member that is disposed on the back surface and fills the wiring substrate so that a part of the wiring substrate is exposed;
    a holding frame that holds the backing member by surrounding a whole circumference on a side of the sideward direction of the backing member, the sideward direction being a direction crossing a direction from the upward direction toward the backward direction; and
    a fixing section that fixes the restricting section to the backing member or the holding section, and thereby prevents wobbling of the wiring substrate and maintains connection between the ultrasound transducer and the wiring substrate.

3. The ultrasound endoscope distal end portion according to claim 1, wherein the restricting section comprises a wiring holding portion that holds the bending portion so that a bending state of the wiring is maintained.

4. The ultrasound endoscope distal end portion according to claim 1, wherein the wiring substrate is bonded and fixed to the restricting section.

5. The ultrasound endoscope distal end portion according to claim 2, wherein the fixing section is a layer of an adhesive, and the restricting section and the backing member or the holding frame are fixed using an adhesive.

6. The ultrasound endoscope distal end portion according to claim 2, further comprising a housing that houses the ultrasound transducer, the wiring substrate, the backing member, the holding frame, the restricting section and the wiring so that the ultrasound transmission/reception surface is exposed,
    wherein the housing comprises a housing side fitting section that fits with the restricting section while in contact with a face on the side of the sideward direction of the restricting section.

7. The ultrasound endoscope distal end portion according to claim 1,
    wherein the restricting section comprises two holders, and the two holders sandwich and fix the wiring substrate so as to cover a connection portion of the plurality of wires electrically connected to the wiring substrate.

* * * * *